US00PP15147P2

(12) United States Plant Patent
Schreurs

(10) Patent No.: US PP15,147 P2
(45) Date of Patent: Sep. 14, 2004

(54) HYBRID TEA ROSE PLANT NAMED 'SCHOLTEC'

(50) Latin Name: *Rosa hybrida*
Varietal Denomination: Scholtec

(75) Inventor: Petrus Nicolaas Johannes Schreurs, De Kwakel (NL)

(73) Assignee: Piet Schreurs Holding BV., De Kwakel (NL)

( * ) Notice: Subject to any disclaimer, the term of this patent is extended or adjusted under 35 U.S.C. 154(b) by 0 days.

(21) Appl. No.: 10/377,522

(22) Filed: Feb. 28, 2003

(51) Int. Cl.[7] ..... A01H 5/00
(52) U.S. Cl. ..... Plt./130
(58) Field of Search ..... Plt./130, 137, 138, Plt./141, 148, 149

*Primary Examiner*—Howard J. Locker
(74) *Attorney, Agent, or Firm*—C. A. Whealy

(57) ABSTRACT

A distinctive cultivar of Hybrid Tea Rose plant named 'Scholtec', characterized by its dark green-colored leaves; vigorous growth habit; long and strong flowering stems; large mauve-colored flowers; high yield of cut flowering stems; and good postproduction longevity.

1 Drawing Sheet

Botanical classification/cultivar designation: *Rosa hybrida* cultivar Scholtec.

BACKGROUND OF THE INVENTION

The present invention relates to a new and distinct cultivar of Hybrid Tea Rose plant, botanically known as *Rosa hybrida*, and hereinafter referred to by the cultivar name Scholtec.

The new cultivar is a product of a planned breeding program conducted by the Inventor in De Kwakel, The Netherlands. The objective of the breeding program was to develop new cut Rose cultivars with a high yield of cut flowering stems, attractive flower color, long and strong stems, dark green leaves and good postproduction longevity.

The new cultivar originated from a cross made by the Inventor in 1999 of two unnamed proprietary selections, not patented. The cultivar Scholtec was discovered and selected by the Inventor as a flowering plant within the progeny of the stated cross in a controlled environment in De Kwakel, The Netherlands. The new cultivar differs primarily from plants of the unnamed proprietary selections in flower color.

Asexual reproduction of the new cultivar by cuttings taken at De Kwakel, The Netherlands, since 2000, has shown that the unique features of the new cultivar are stable and reproduced true to type in successive generations of asexual reproduction.

SUMMARY OF THE INVENTION

The following traits have been repeatedly observed and are determined to be the unique characteristics of 'Scholtec'. These characteristics in combination distinguish the new Hybrid Tea Rose as a new and distinct cultivar:

1. Dark green-colored leaves.
2. Vigorous growth habit.
3. Long and strong flowering stems.
4. Large mauve-colored flowers.
5. High yield of cut flowering stems.
6. Good postproduction longevity.

Plants of the new Hybrid Tea Rose can be compared to plants of the cultivar Schrenat, disclosed in U.S. Plant patent application Ser. No 10/109,950. In side-by-side comparisons conducted in De Kwakel, The Netherlands, plants of the new Hybrid Tea Rose differed from plants of the cultivar Schrenat in the following characteristics:

1. Plants of the new Hybrid Tea Rose were taller and broader than plants of the cultivar Schrenat.
2. Flowers of plants of the new Hybrid Tea Rose were mauve in color whereas flowers of plants of the cultivar Schrenat were pink in color.

BRIEF DESCRIPTION OF PHOTOGRAPHS

The accompanying colored photographs illustrate the new Hybrid Tea Rose plant showing the colors as true as it is reasonably possible to obtain in colored reproduction of this type. Colors in the photographs may differ slightly from the color values cited in the detailed botanical description which accurately describe the actual colors of the new Hybrid Tea Rose.

The photograph at the top of the sheet comprises a side perspective view of typical flowers of the new Hybrid Tea Rose.

The photograph at the bottom of the sheet comprises a top perspective view of the upper surface (left) and the lower surface (right) of typical leaves of the new Hybrid Tea Rose.

DETAILED BOTANICAL DESCRIPTION

Plants of the new Hybrid Tea Rose have not been observed under all possible environmental conditions. The phenotype may vary significantly with variations in environment such as temperature and light without, however, any variance in genotype.

The aforementioned photographs, following observations and measurements describe plants grown in De Kwakel, The Netherlands, in glass-covered greenhouses with an average day temperature of 19° C. and an average night temperature of 15° C. Plants used for the photographs and the description were about five months old. In the following description, color references are made to The Royal Horticultural Society Colour Chart, 1995 Edition, except where general terms of ordinary dictionary significance are used.

Classification:

*Botanical.*—*Rosa hybrida* cultivar Scholtec.

*Commercial.*—Hybrid Tea Rose used as a cut flower.

Parentage:

*Female, or seed, parent.*—Unnamed proprietary selection of *Rosa hybrida*, not patented.

*Male, or pollen, parent.*—Unnamed proprietary selection of *Rosa hybrida*, not patented.

Propagation:

*Type.*—By vegetative cuttings.

*Time to initiate roots.*—About 12 days at 25° C.

*Time to develop roots.*—About 25 days at 25° C.

*Root description.*—Fine, fibrous and well-branched.

Plant description:

*Form.*—Upright.

*Plant height.*—About 100 to 110 cm.

*Plant width.*—About 110 to 120 cm.

*Growth habit.*—Vigorous.

*Yield of flowering stems.*—In one year, about 160 flowering stems per square meter can be harvested per plant.

*Flowering stems.*—Quantity per plant: About 10 to 12 per plant. Aspect: Straight, upright. Strength: Strong. Length: About 80 to 90 cm. Diameter: About 2 cm. Internode length: About 4 to 8 cm. Texture: Glabrous. Color: 146A. Thorns: Quantity: About one per 1 cm of stem length. Height: About 7 to 8 mm. Diameter, at base: About 7 to 10 mm. Shape: Triangular. Color: 174A.

*Foliage description.*—Arrangement: Alternate; compound with about 3 to 7 leaflets. Quantity per flowering stem: About 15 compound leaves. Leaf length: About 15 to 20 cm. Leaf width: About 12 to 15 cm. Terminal leaflet length: About 9 to 11 cm. Terminal leaflet width: About 6 to 8 cm. Lateral leaflet length: About 6 to 8 cm. Terminal leaflet width: About 5 to 6 cm. Leaflet shape: Ovate to oval. Leaflet apex: Rounded. Leaflet base: Obtuse. Leaflet margin: Serrulate. Leaflet texture, upper and lower surfaces: Glabrous; leathery. Leaflet venation pattern: Pinnate. Leaf petiole length: About 2 to 3 cm. Leaf petiole diameter: About 2 mm. Leaflet petiole length: About 1 to 2 cm. Leaflet petiole diameter: About 1 to 2 mm. Stipules: Length: About 2 cm. Diameter: About 1 cm. Shape: Roughly lanceolate. Apex: Cleft. Base: Cuneate. Texture, upper and lower surfaces: Glabrous; leathery. Color: Developing and fully expanded foliage, upper surface: Darker than 147A. Developing and fully expanded foliage, lower surface: 147B. Venation, upper surface: 195A. Venation, lower surface: 146D. Leaf and leaflet petioles, upper and lower surfaces: 146B. Stipule, upper surface: 137B. Stipule, lower surface: 144B.

Flower description:

*Flower type and habit.*—Large mauve-colored flowers; symmetrical rosette flowers. Freely and recurrent flowering habit. Flowers arranged singly at terminal apices or in sprays. Flowers persistent.

*Flowering season/time to flower.*—Year-round under greenhouse conditions.

*Flower diameter.*—About 7 to 11 cm.

*Flower depth (height).*—About 5 to 6 cm.

*Flower longevity on plant.*—About three weeks.

*Flower longevity as a cut flower.*—About two weeks.

*Fragrance.*—Slight, typical rose fragrance.

*Flower buds (at stage of showing color).*—Shape: Ovoid. Length: About 4 to 5 cm. Diameter: About 3 to 4 cm. Color: 54A.

*Petals.*—Quantity: About 40 per flower arranged in numerous whorls. Length: About 4.2 to 6 cm. Width: About 5.3 to 7.5 cm. Shape: Obovate. Apex: Rounded. Margin: Entire. Texture: Smooth, satiny. Color: When opening, upper surface: 75B; towards the base, 2D. When opening, lower surface: 75C; towards the base, 2D. Fully opened, upper surface: 70C; towards the base, 2D; color becoming closer to 75A with development. Fully opened, lower surface: 72D; towards the base, 2D.

*Sepals.*—Quantity per flower: Five. Length: About 2.5 cm. Width: About 1.2 cm. Shape: Lanceolate. Apex: Apiculate. Base: Cuneate. Margin: Entire. Texture, upper and lower surfaces: Pubescent. Color: Upper surface: 145A. Lower surface: 145C.

*Peduncles.*—Strength: Strong. Aspect: Erect. Length: About 9 to 10 cm. Diameter: About 6 to 7 mm. Texture: Glabrous. Color: 144A.

*Reproductive organs.*—Stamens: Quantity per flower: About 100. Anther length: About 4 mm. Anther shape: Elliptic. Anther color: 4C. Filament color: 4D. Pistils: Quantity per flower: About 150. Pistil length: About 6 mm. Stigma shape: Elliptic. Stigma color: 28B. Style length: About 5 mm. Style color: 4D. Receptacle height: About 1.3 to 1.5 cm. Receptacle diameter: About 1.7 to 1.9 cm. Receptacle color: 144A.

*Seed/fruit.*—Seed and fruit development has not been observed.

Disease/pest resistance: Plants of the new Hybrid Tea Rose have not been observed to be resistant to pathogens and pests common to roses.

It is claimed:

1. A new and distinct Hybrid Tea Rose plant named 'Scholtec', as illustrated and described.

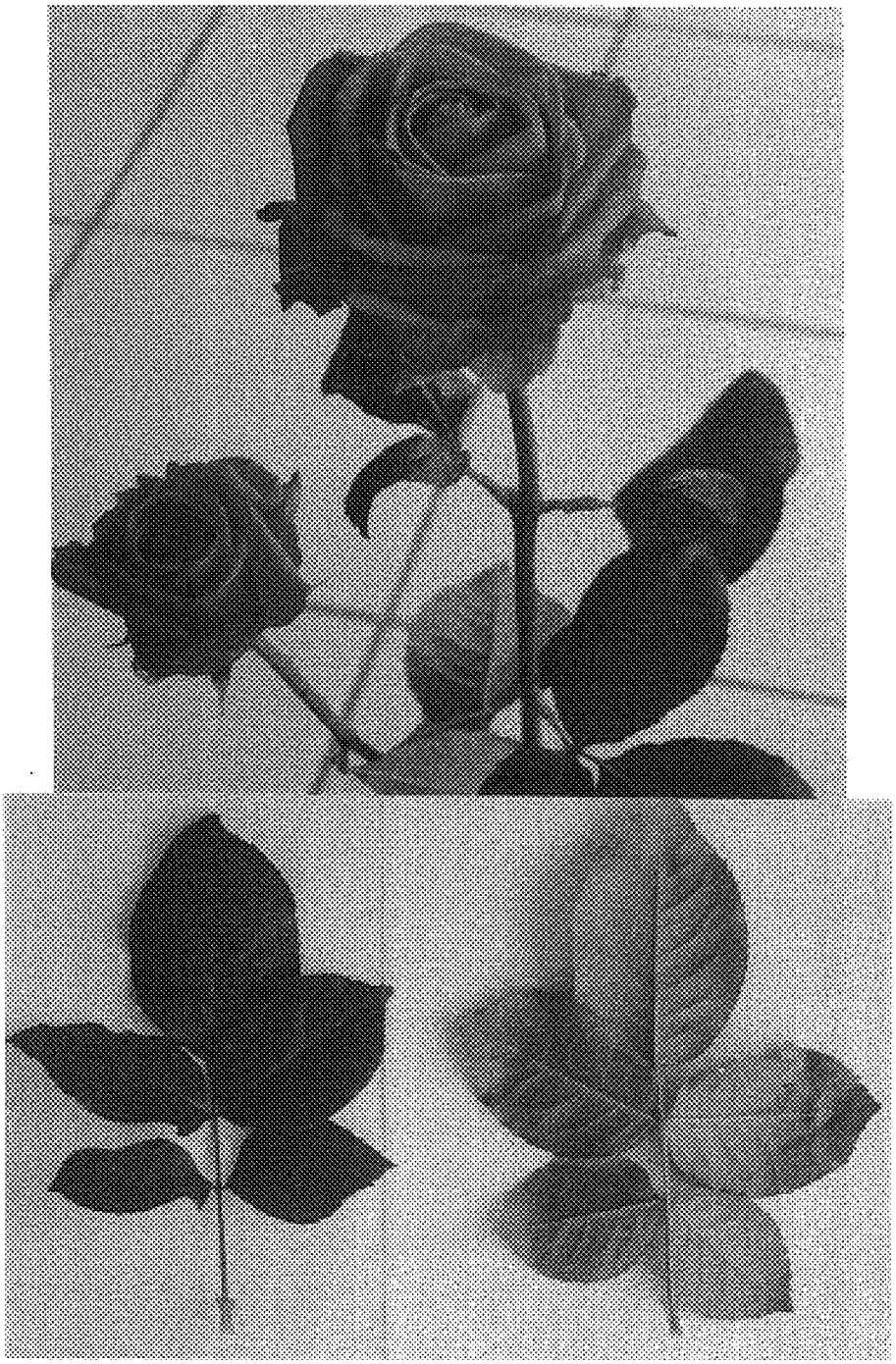

* * * * *